US010564154B2

(12) United States Patent
Davis et al.

(10) Patent No.: US 10,564,154 B2
(45) Date of Patent: Feb. 18, 2020

(54) CAPACITANCE SPECTROSCOPIC METHOD AND ELECTRODE

(71) Applicants: Oxford University Innovation Limited, Oxford (GB); Universidade Estadual Paulista "Julio de Mesquita Filho"—UNESP, São Paulo (BR)

(72) Inventors: Jason Davis, Oxford (GB); Paulo Roberto Bueno, São Paulo (BR)

(73) Assignees: Oxford University Innovation Limited, Oxford (GB); Universidade Estadual Paulista "Julio de Mesquita Filho"—UN-ESP, Sao Paulo (BR)

( * ) Notice: Subject to any disclaimer, the term of this patent is extended or adjusted under 35 U.S.C. 154(b) by 588 days.

(21) Appl. No.: 14/912,017

(22) PCT Filed: Jun. 25, 2014

(86) PCT No.: PCT/GB2014/051938
§ 371 (c)(1),
(2) Date: Feb. 12, 2016

(87) PCT Pub. No.: WO2015/022483
PCT Pub. Date: Feb. 19, 2015

(65) Prior Publication Data
US 2016/0195520 A1    Jul. 7, 2016

(30) Foreign Application Priority Data
Aug. 12, 2013   (GB) .................................. 1314402.7

(51) Int. Cl.
*G01N 33/551*   (2006.01)
*G01N 33/543*   (2006.01)
(Continued)

(52) U.S. Cl.
CPC ....... *G01N 33/5438* (2013.01); *G01N 27/026* (2013.01); *G01N 27/27* (2013.01);
(Continued)

(58) Field of Classification Search
CPC ............. G01N 27/026; G01N 27/3276; G01N 33/5438; G01N 27/27; G01N 27/3277;
(Continued)

(56) References Cited

U.S. PATENT DOCUMENTS 4,020,830 A * 5/1977 Johnson .............. A61B 5/14532
                                                           600/348
4,220,450 A * 9/1980 Maggio ................ G01N 33/581
                                                           435/5
(Continued)

FOREIGN PATENT DOCUMENTS

WO     98/57159 A1    12/1998
WO  2011/069997 A2     6/2011
(Continued)

OTHER PUBLICATIONS

Berggren et al., "Capacitive Biosensors," *Electroanalysis* 13(3):173-180, 2001.
(Continued)

*Primary Examiner* — Christopher L Chin
(74) *Attorney, Agent, or Firm* — Klarquist Sparkman, LLP (57) ABSTRACT

Capacitance spectroscopic method and electrode The application relates to methods and electrodes for electrochemical detection of target species by capacitance spectroscopy. The method is simple, frequency optimised and extremely sensitive to low concentrations of target species. The electrodes of the invention can easily be reused and are ideally suited for use in point-of-care diagnostics.

7 Claims, 4 Drawing Sheets

(51) Int. Cl.
  *G01N 27/02* (2006.01)
  *G01N 27/327* (2006.01)
  *G01N 27/27* (2006.01)
  *G01N 33/68* (2006.01)
(52) U.S. Cl.
  CPC ..... *G01N 27/3276* (2013.01); *G01N 27/3277* (2013.01); *G01N 33/54353* (2013.01); *G01N 33/68* (2013.01); *G01N 2333/4737* (2013.01)
(58) Field of Classification Search
  CPC ............. G01N 33/54353; G01N 33/68; G01N 2333/4737
  See application file for complete search history.

(56) References Cited

U.S. PATENT DOCUMENTS

| | | | | |
|---|---|---|---|---|
| 5,057,313 | A * | 10/1991 | Shih | A61K 49/085 424/1.53 |
| 5,223,117 | A | 6/1993 | Wrighton et al. | |
| 9,063,156 | B2 * | 6/2015 | Korlach | C12Q 1/6825 |
| 2004/0099531 | A1 * | 5/2004 | Srinivasan | G01N 33/5438 204/412 |
| 2005/0196820 | A1 * | 9/2005 | Zweig | C12Q 1/004 435/14 |
| 2006/0115857 | A1 * | 6/2006 | Keen | B82Y 10/00 435/7.1 |
| 2009/0250343 | A1 * | 10/2009 | Moon | C12Q 1/001 204/403.14 |
| 2011/0139636 | A1 | 6/2011 | Lai et al. | |
| 2012/0073986 | A1 * | 3/2012 | Jackson | C12Q 1/001 205/775 |
| 2012/0199499 | A1 * | 8/2012 | O—Connor | B82Y 15/00 205/777.5 |
| 2012/0228155 | A1 * | 9/2012 | Clare | G01N 27/3277 205/777.5 |
| 2013/0112572 | A1 * | 5/2013 | Bertin | C12Q 1/004 205/777.5 |
| 2014/0005068 | A1 * | 1/2014 | Das | G01N 27/3277 506/9 |
| 2014/0106441 | A1 * | 4/2014 | Wang | C12Q 1/689 435/287.2 |
| 2016/0186229 | A1 * | 6/2016 | Hall | G01N 27/3271 435/14 |

FOREIGN PATENT DOCUMENTS

| | | |
|---|---|---|
| WO | 2012/097081 A2 | 7/2012 |
| WO | 2013/029114 A1 | 3/2013 |

OTHER PUBLICATIONS

Bryan et al., "An optimised electrochemical biosensor for the label-free detection of C-reactive protein in blood," *Biosensors and Bioelectronics*, pp. 1-5, 2012.
Bryan et al., "The robust electrochemical detection of a Parkinson's disease marker in whole blood sera," *Chemical Science* 3:3468-3473, 2012.
Bueno et al., "Capacitance Spectroscopy: A Versatile Approach to Resolving the Redox Density of States and Kinetics in Redox-Active Self Assebled Monolayers," *J. Phys. Chem. B* 116:8822-8829, 2012.
Bueno et al., "Elucidating Capacitance and Resistance Terms in Confined Electroactive Molecular Layers," *Analytical Chemistry* 85:411-417, 2013.
Dominici et al., "Measurement of C-reactive Protein: Two High Sensitivity Methods Compared," *Journal of Clinical Laboratory Analysis* 18:280-284, 2004.
Eckermann et al., "Electrochemistry of redox-active self-assembled monolayers," *Coord Chem Rev* 254(15-16):1769-1802, 2010. (95 pages).
Elliott et al., "Electronically Conducting Poly-Tris(5,5'-BIS[(3-Acrylyl-1-Propoxy)Carbonyl]-2,2'-Bipyridine)Ruthenium-Modified Electrodes—Studies of Bilayer Films and Solution Redox Reactions," *J. Electroanal. Chem.* 213:203-215, 1986.
Fernandes et al., "Label free redox capacitive biosensing," *Biosensors and Bioelectronics* 50:437-440, 2013.
Goes et al., "A Dielectric Model of Self-Assembled Monolayer Interfaces by Capacitive Spectroscopy," *Langmuir* 28:9689-9699, 2012.
Gooding et al., "The Rise of Self-Assembled Monolayers for Fabricating Electrochemical Biosensors—An Interfacial Perspective," *The Chemical Record* 12:92-105, 2012.
International Search Report and Written Opinion, dated Sep. 22, 2014, for International Application No. PCT/GB2014/051938, 8 pages.
Katz et al., "Probing Biomolecular Interactions at Conductive and Semiconductive Surfaces by Impedance Spectroscopy: Routes to Impedimetric Immunosensors, DNA—Sensors, and Enzyme Biosensors," *Electroanalysis* 15(11):913-947, 2003.
Khor et al., "The importance of interfacial design for the sensitivity of a label-free electrochemical immuno-biosensor for small organic molecules," *Biosensors and Bioelectronics* 26:2038-2044, 2011.
Liu et al., "Protein modulation of electrochemical signals: application to immunobiosensing," *Chem. Commun.*, pp. 3870-3872, 2008.
Liu et al., "Development of an electrochemical immunosensor for the detection of HbA1c in serum," *Analyst* 137:829-832, 2012.
Oliveira et al., "Primary Structure of Human C-reactive Protein," *The Journal of Biological Chemistry* 254(2):489-502, 1979.
Patents Act 1977: Search Report under Section 17, dated Jan. 30, 2014, for Great Britain Application No. GB1314402.7, 1 page.
Pepys et al., "Acute Phase Proteins with Special Reference to C-Reactive Protein and Related Proteins (Pentaxins) and Serum Amyloid A Protein," *Advances in Immunology* 34:141-212, 1983.
Pepys et al., "C-reactive protein: a critical update," *J. Clin. Invest.* 111:1805-1812, 2003.
Rodriguez et al., "Aptamer biosensor for based on recognition-induced switching label-free impedance spectroscopy detection of proteins of the surface charge," *Chem. Commun.*, pp. 4267-4269, 2005.
Sumner et al., "Redox Kinetics in Monolayers on Electrodes: Electron Transfer Is Sluggish for Ferrocene Groups Buried within the Monolayer Interior," *J. Phys. Chem. B* 105:8739-8745, 2001.
Trasatti et al., "Real Surface Area Measurements in Electrochemistry," *Pure & Appl. Chem.* 63(5):711-734, 1991.
Zhang et al., "Development of a spiral piezoelectric immunosensor based on thiol self-assembled monolayers for the detection of insulin," *Journal of Immunological Methods* 338:7-13, 2008.

* cited by examiner

CAPACITANCE SPECTROSCOPIC METHOD AND ELECTRODE

The present invention relates to methods and electrodes for the electrochemical detection of a target species by capacitance spectroscopy.

BACKGROUND

A number of commercial assay techniques are based on the biorecognition of a target species by a suitable receptor species. One area of particular interest arises where the target species is a biomarker, namely a substance whose presence in a biological sample might be measured and evaluated as an indicator of normal biological processes, pathogenesis, or a pharmacological response to therapeutic intervention. For example, assay techniques capable of detecting protein biomarkers can be of substantial clinical value, given their intimate association with current biological function.

Accordingly, the quantified detection of biomarkers in biological media, such as blood sera, holds enormous promise both for the early detection of disease or physiological misfunction and for the subsequent tracking of disease progression in response to therapy. A consensus is emerging that early detection and personalized treatment in clinics, based on genetic and proteomic profiles of perhaps four to twenty key biomarkers, could give rise to substantial improvements in the survival rates of patients suffering from a range of complex infectious, autoimmune, cancer and cardiac diseases.

A wide variety of strategies, such as those based on enzyme-linked immunosorbent assay (ELISA), surface plasmon resonance (SPR) and electroanalysis, have already been developed with the aim of achieving selective detection of different biomarkers.

In many such assay systems, some form of labelling (e.g., radioactive, enzymatic or fluorescent labelling) is an essential prerequisite for achieving the necessary selectivity and sensitivity in the biorecognition event and its subsequent reporting. Unfortunately, labelling can be associated with numerous problems, such as cost issues, impractical assay timescales, potential perturbations caused by the label and the generation of non-specific signals.

On the other hand, label-free methods are also associated with significant practical challenges, including the need for much greater sensitivity to the underlying biorecognition event (a consequence of the absence of a label that is specifically designed to respond strongly when the biorecognition event takes place), while nonetheless retaining high specificity to the target species.

A number of label-free methods based on electrochemical techniques have, nonetheless, been developed. In very general terms, an electrical biosensor reports on the capturing of a biological species by an electrode-confined corresponding receptor species through a current or voltage signal (or a perturbation thereof) generated at the electrode.

In principle, a number of different electrochemical techniques might be utilised, in each case resulting in the interrogation of different aspects of the electrochemical properties of the electrode and its local environment. For example, voltammetric methods have been proposed whereby the current response to an applied voltage is measured on a system in which a receptor such as an antibody is confined to the electrode surface. Such methods have an advantage in terms of their conceptual simplicity, but they do not necessarily provide satisfactory selectivity or sensitivity for biomarkers present at inherent very low levels in biological samples.

A different approach makes use of electrochemical impedance spectroscopy (EIS), which is a technique that monitors changes in capacitance or charge-transfer resistance associated with the specific binding of certain materials to a suitably modified electrode surface.

Two distinct classes of EIS methods can be distinguished. In "non-faradaic EIS", no external redox active probe is typically added to the system and so the signal response reflects purely non-faradaic impedance characteristics. On the other hand, in "faradaic EIS" a discrete, typically solution-phase, redox probe is added in large excess to the system. Generally, this is done with the aim of increasing signal magnitude, on the basis that the resistive effects of the biorecognition event at the electrode surface should be amplified by sampling the impact of the biorecognition on the current generated by the redox probe.

Although EIS-based techniques have the potential to give rise to highly sensitive and specific assays, they can suffer from problems associated, for example, with the modelling assumptions inherent in signal analysis (conventional analysis relies on fitting the experimental data using a simple Randles-like circuit model). In addition, still further improvements in sensitivity and selectivity would be desirable. Ideally this would also be achievable without the need to add a redox probe to the analytical solution.

As a result, there remains a need for the provision of further assay methods suitable for the detection of target species such as biomarkers. Of particular value would be methods that are robust and not reliant on modelling assumptions, which are highly selective to the target species of interest and which have sensitivities that compare favourably, and preferably surpass, those achievable with current state-of-the-art methods.

SUMMARY OF THE INVENTION

The present inventors have now found that an electrochemical technique based on capacitance spectroscopy (a recently identified modification of EIS), when carried out using a specially designed electrode on which are disposed both first moieties comprising redox active probes and second moieties comprising suitable receptors, is capable of providing extremely selective and sensitive detection of target species, including biomarkers of direct clinical significance. The methodology is simple, frequency optimised (and therefore readily applicable to multiplexing strategies) and does not rely on any modelling assumptions for data analysis purposes. Moreover, detection sensitivities may extend as far down as the picomolar range. Still further, the electrodes can easily be reused and so are ideally suited for use in point-of-care diagnostics.

The present invention thus provides a method for electrochemical detection of a target species, which method comprises: (A) contacting a carrier medium comprising said target species with an electrode, wherein said electrode has a surface on which are disposed first moieties and second moieties, wherein each of said first moieties comprises a redox active probe and each of said second moieties comprises a receptor capable of binding selectively to said target species; (B) obtaining a first measurement of complex impedance by electrochemical impedance spectroscopy at a first applied potential that is within the redox window of said redox active probe; and (C) obtaining a second measurement of complex impedance by electrochemical impedance spectroscopy at a second applied potential that is different from said first applied potential.

The present invention also provides an electrode for use in the electrochemical detection of a target species, wherein the electrode has a surface on which are disposed first moieties and second moieties, wherein each of said first moieties comprises a redox active probe and each of said second moieties comprises a receptor capable of binding selectively to said target species.

Still further, the present invention provides a method of making an electrode of the present invention, which method comprises disposing, on the surface of an electrode substrate, (i) first moieties that each comprise a redox active probe and (ii) second moieties that each comprise a receptor capable of binding selectively to a target species. In addition, the present invention provides an electrode obtainable by carrying out this method.

The present invention additionally provides an electrochemical spectrometer comprising an electrode of the present invention.

The present invention also provides use of an electrode of the present invention for electrochemical detection of a target species.

Further preferred features and embodiments are described in the accompanying description and the appended claims.

BRIEF DESCRIPTION OF THE FIGURES

FIG. 5 depicts complex molecular film capacitance for the system of the Example, at electrode potentials corresponding to the ferrocene reporter half wave potential ("redox in") or outside the ferrocene reporter redox window ("redox out"). Graph a) shows the real part of the complex capacitance (C'), whereby for the "redox in" lines, the top line corresponds to immunoassay working electrodes modified with anti-CRP in the test solutions that do not contain CRP target, and the progressively lower lines correspond to progressively increasing concentrations of CRP target in the test solutions, as indicated. Graph b) shows analogous response of the imaginary part of the complex capacitance (C"); again the top line of the "redox in" group corresponds to a test solution containing no CRP target, with progressively lower lines corresponding to progressively increasing concentrations of CRP target in the test solutions, as indicated. All plots on both graphs are average curves obtained from three different immunoassay working electrodes.

DETAILED DESCRIPTION

Optional and preferred features of the present invention are now described. Any of the features described herein may be combined with any of the other features described herein, unless otherwise stated.

The Electrode

The electrode of the invention (which, for the avoidance of doubt, is the electrode used in the methods and uses of the present invention), has a surface on which are disposed first moieties and second moieties. Each of said first moieties comprises a redox active probe. Each of said second moieties comprises a receptor capable of binding selectively to a target species of interest (e.g. a biomarker).

The electrode comprises an electrode substrate. The first and second moieties are disposed on the surface of this substrate. The substrate may comprise any electrically conducting material. The substrate may comprise a metal or carbon. The metal may be a metal in elemental form or an alloy of a metal. Optionally, the whole of the substrate comprises a metal or carbon. The substrate may comprise a transition metal. The substrate may comprise a transition metal selected from any of groups 9 to 11 of the Periodic Table. The substrate may comprise a metal selected from, but not limited to, rhenium, iridium, palladium, platinum, copper, indium, rubidium, silver and gold. The substrate may comprise a metal selected from gold, silver and platinum. The substrate may comprise a carbon-containing material, which may be selected from edge plane pyrolytic graphite, basal plane pyrolytic graphite, glassy carbon, boron doped diamond, highly ordered pyrolytic graphite, carbon powder and carbon nanotubes.

In a preferred embodiment, the substrate comprises gold, for example the substrate is a gold substrate.

The electrode surface (i.e., the substrate surface) is preferably planar, which includes a generally flat surface, typically without indentations, protrusions and pores. Such substrate surfaces can be readily prepared by techniques such as polishing with fine particles, e.g. spraying with fine particles, optionally in a sequence of steps where the size of the fine particles is decreased in each polishing step. The fine particles may, for example, comprise a carbon-based material, such as diamond, and/or may have particles with diameters of 10 µm or less, optionally 5 µm or less, optionally 3 µm or less, optionally 1 µm or less, optionally 0.5 µm or less, optionally 0.1 µm or less. Following polishing, the substrate surface may be washed, e.g. ultrasonically, optionally in a suitable liquid medium, such as water, e.g. for a period of at least 1 minute, e.g. from about 1 minute to 10 minutes. Optionally, the substrate surface may be washed with an abrasive, e.g. acidic, solution, for example following the polishing and, if used, ultrasonic washing steps. The abrasive solution may comprise an inorganic acid, e.g. $H_2SO_4$, and/or a peroxide, e.g. $H_2O_2$, in a suitable liquid medium, e.g. water. Optionally, the substrates can be electrochemically polished, which may follow any steps involving one or more of polishing with fine particles, washing e.g. ultrasonically and/or using an abrasive solution. The electrochemical polishing may involve cycling between an upper and lower potential until a stable reduction peak is reached, e.g. an upper potential of 0.5 V or more, optionally 1 V or more, optionally 1.25 V or more, and a lower potential of 0.5 V or less, optionally 0.25 V or less, optionally 0.1 V or less.

The first moieties disposed on the electrode surface each comprise a redox active probe. A redox active probe is a substance that is capable of undergoing a change in oxidation state, with the concomitant gain or loss of at least one electron, in response to an applied potential. The skilled person would be able to select a suitable redox active probe for use in a given electrode of the present invention. For example, any chemically stable reporter can be used that can be readily assembled at surfaces and that exhibits a good redox response (i.e, a strong signal) within a non-destructive/non interfering potential window.

Representative examples of particularly suitable redox active probes include osmium-based redox systems, ferrocenes, quinones and porphyrins, including derivatives thereof. Derivatives of quinine include p-benzoquinone and hydroquinone. Preferably the redox active probe is ferrocene or a derivative thereof, for example an alkyl (e.g., $C_{1-6}$ alkyl) or acyl derivative thereof. Most preferably the redox active probe is ferrocene.

By "disposed on the electrode surface" is meant that the association between the first moieties and the electrode surface is sufficiently stable that the first moieties do not become detached from the electrode surface in the presence of the carrier medium. The first moieties may be disposed on the electrode surface by covalent attachment or by non-covalent attachment. For the avoidance of doubt, it is emphasised that the association formed, for example, between a gold electrode surface and a thiol group comprised by a first moiety is regarded as being a covalent attachment. Indeed, this constitutes an exemplary means of disposing the first moieties on the electrode surface.

When the redox active probe is itself capable of becoming disposed on the electrode surface (i.e., of forming the stable association defined above), then the first moiety may consist of the redox active probe alone. For example, a redox active probe carrying a thiol group is inherently capable of forming a stable association with an electrode surface such as that of a gold electrode.

Alternatively, and preferably, the first moiety may be attached to the surface of the substrate via a linker species. If a linker species is present on the surface of the substrate, the linker species may for example comprise a self-assembling monolayer or may comprise a self-assembling monolayer-anchored polymer.

In an embodiment, the first moiety is of the formula $A_1$-$L_1$-RAP, wherein $A_1$ is a moiety bound to the surface of the substrate, $L_1$ is a linker moiety and RAP is the redox active probe (e.g., as defined elsewhere herein).

$A_1$ may be selected from any appropriate binding group, depending on the nature of the material of the substrate. For example, $A_1$ may be selected from, but is not limited to, biotin, hydrazine, alkynyl, alkylazide, amino, hydroxyl, carboxy, thio, aldehyde, phosphoinothioester, maleimidyl, succinyl, succinimidyl, isocyanate, ester, strepavidin, avidin, neuavidin, and biotin binding proteins. If the electrode substrate comprises a noble material, e.g. gold, silver or platinum, $A_1$ is preferably thiol (or thiolate), which may be selected from —SH and —S—. If the substrate comprises a metal that has a layer of oxide on its surface, e.g. copper, A may be a carboxy group.

$L_1$ may be any species that links to $A_1$ and also links to RAP. In this context "links" includes "covalently links" and "non-covalently links", for example via a stable hydrophobic interaction. Furthermore, "links" implies a stable linkage between any two respective groups, wherein stable means that the linkage does not break in the presence of the carrier medium (e.g., a liquid medium, such as a biological fluid selected for example from blood, urine, tears, saliva, sweat, and cerebrospinal fluid). Preferably, however, $L_1$ is covalently linked both to $A_1$ and to RAP, i.e. it covalently links $A_1$ to RAP.

$L_1$ is preferably a species that allows formation of a self-assembling monolayer. For example, $L_1$ may be a hydrocarbon moiety. $L_1$ may comprise an alkyl moiety comprising at least 2 carbons, the alkyl moiety being directly attached to $A_1$; optionally the alkyl moiety is a straight-chain alkyl moiety. $L_1$ may comprise an alkyl moiety comprising at least 10 carbons, optionally from 10 to 30 carbons, optionally from 10 to 20 carbons, optionally from 11 to 15 carbon atoms, and the alkyl moiety is optionally a straight-chain alkyl moiety, and the alkyl moiety is directly attached to $A_1$.

For the avoidance of doubt, the terms "alkylene" and "alkyl" may be used interchangeably throughout this is specification because it is clear from context how many hydrogen atoms of the corresponding (parent) alkane must be removed in order for the group to be attached to other specified functional groups. For example, the group $L_1$ may typically be covalently attached at least to the group $A_1$, implying that at least one carbon atom has been removed from the corresponding alkane. Whether the group $L_1$ is also covalently (rather than non-covalently) attached to the group RAP, this implies that in total at least two (e.g., two) carbon atoms have been removed from the corresponding alkane.

In an embodiment, $L_1$ is of the formula —$(CH_2)_{n1}$—(—O—$CH_2$—$CH_2$—)$_{m1}$-$D_1$-, wherein n1 is from 1 to 30 and m1 is from 0 to 10 and $D_1$ is a bond or a group bound to RAP. $D_1$ may for example be selected from a bond or —(C=O)—, —$OCH_2$—(C=O)—, —(C=O)—NH—, —(C=O)—O—, —$OCH_2$—(C=O)—NH—, —$OCH_2$—(C=O)—OH—, —O— or —NH—. n1 may for example be from 10 to 20. m1 may for example be 1 to 5, optionally 2 to 4, optionally 3. Optionally, if $D_1$ is any one of the species (C=O)—NH—, —(C=O)—O—, —$OCH_2$—(C=O)—NH—, —$OCH_2$—(C=O)—O—, —O— and —NH—, then —NH— or —O— in these species may be derived from a redox active agent, prior to being bound to the linker species $L_1$.

In an embodiment, $A_1$-$L_1$- is a species of formula thiol-$(CH_2)_{n1}$—$(-O-CH_2-CH_2-)_{m1}$-$D_1$- wherein n1 is from 1 to 30 and m1 is from 0 to 10 and $D_1$ is a group that binds to RAP; optionally n1, m1 and $D_1$ may be as defined above, and thiol is selected from —S— and HS—.

In another embodiment, the first moiety may comprise a polymer that is attached both to: (a) the surface of the electrode; and (b) the redox active probe. Preferably said polymer comprises a plurality of pendant betaine or other hydrophilic and/or zwitterionic monomer groups. A betaine group is a group that comprises both a positively charged cationic functional group that bears no hydrogen atom (e.g., a quaternary ammonium or phosphonium functional group) and a negatively charged functional group (for example a carboxylate group or a sulfonate group). Pendant means that the said betaine groups are side groups extending away from the main chain of the polymer (i.e., the chain derived from repeating monomeric units).

The pendant betaine groups may, for example, each comprise a quaternary ammonium cation and a carboxylate group. For example, the pendant betaine groups may have the formula (I)

wherein:
$R_1$ and $R_3$ are the same or different and are each a $C_1$ to $C_5$ alkylene group;
$R_2$ and $R_{2'}$ are the same or different and are each a $C_1$ to $C_5$ alkyl group; and X is O or NH.

In one exemplary aspect the pendant betaine groups may have the formula (I) wherein $R_1$ and $R_3$ are ethylene, $R_2$ and $R_{2'}$ are methyl and X is O. A polymer containing such pendant groups can be obtained by photopolymerisation of carboxybetaine (alkyl)acrylates such as carboxybetaine methylacrylate (CBMA) and carboxybetaine ethylacrylate (CBEA). In another exemplary aspect the pendant betaine groups may have the formula (I) wherein $R_1$ is propylene, $R_3$ is ethylene, $R_2$ and $R_{2'}$ are methyl and X is NH. A polymer containing such pendant groups can be obtained by photopolymerisation of carboxybetaine (alkyl)acrylamides such as carboxybetaine acrylamide.

The polymer may for example have a hydrocarbon main chain, for example a main chain that is a straight chain or branched chain alkylene moiety (e.g., having at least 10 carbon atoms, optionally at least 50 carbon atoms, optionally at least 100 carbon atoms). Typically where the polymer comprises a plurality of pendant betaine groups the polymer comprises at least 5, or at least 10, for example at least 25 pendant betaine groups. Such polymers are for example obtainable by photopolymerisation of photopolymerisable monomers containing a photopolymerisable carbon-carbon double bond (as well as a betaine group, should the polymer comprise a plurality of pendant betaine groups). For example, monomers comprising (alkyl)acrylate groups such as acrylate, methacrylate and ethyacrylate can be used.

The second moieties disposed on the electrode surface each comprise a receptor capable of binding selectively to a target species. Capable of binding specifically to a target species typically means having a binding constant to the target species at least 50 times greater than the binding constant to any other species present in the carrier medium, preferably at least 100 times greater and more preferably still at least 200 times greater.

The receptor preferably comprises or is a species selected from an antibody, an antibody fragment, an aptamer, an oligosaccharide, a peptide, and a protein. Preferably, the receptor comprises or is a species selected from an antibody, a nucleic acid and a peptide. Most preferably the receptor comprises or is an antibody, e.g. it is an antibody.

The antibody or the antibody fragment may be selected from one or more of the classes IgA, IgD, IgE, IgG and IgM. In a preferred embodiment, the antibody or antibody fragment is of the IgG type. The antibody binds selectively to the target species. The antibody or antibody fragment may be derived from a mammal, including, but not limited to, a mammal selected from a human, a mouse, a rat, a rabbit, a goat, a sheep, and a horse. In an embodiment, the receptor comprises an antibody of the IgG type derived from a mouse.

The aptamer may be selected from a peptide aptamer, a DNA aptamer and a RNA aptamer.

Clearly, the choice of receptor for a given electrode is determined by the identity of the target species of interest.

Suitable target species include proteins, polypeptides, antibodies, nanoparticles, drugs, toxins, harmful gases, hazardous chemicals, explosives, viral particles, cells, multicellular organisms, cytokines and chemokines, ganietocyte, organelles, lipids, nucleic acid sequences, oligosaccharides, chemical intermediates of metabolic pathways and macromolecules. In preferred embodiments, the target species comprises, consists essentially of, or consists of, a biological molecule, more suitably a biological macromolecule, most suitably a polypeptide. A biomarker is one example of a biological molecule of particular interest.

If the target species is or comprises a protein, the protein may be selected from, but is not limited to, native proteins, denatured proteins, protein fragments, and prokaryotically or eukaryotically expressed proteins. Protein may have its normal meaning in the art, and most preferably 'protein' refers to a polypeptide molecule. Such polypeptide may comprise modifications such as glycosylation; phosphorylation or other such modifications.

If the target species is an antibody, the antibody may be selected from one or more of the classes IgA, IgD, IgE, IgG and IgM.

If the target species is a nanoparticle, the nanoparticle can be selected from, but is not limited to, one or more of insulating, metallic or semiconducting nanoparticles.

If the target species is a drug, the drug may be selected from, but is not limited to, alcohol (e.g. ethanol), amphetamines, amyl nitrate, heroin, ketamine, anabolic steroids, LSD, solvents, cannabis, cocaine (such as cocaine hydrochloride or 'coke'), tobacco, tranquilisers, crack (i.e. cocaine free base), ecstasy and/or gammhydroxybutyrate (GHB). Alternatively, in some embodiments, the drug may be a medicinal substance.

The target species may be a candidate drug, e.g. a chemical or biological entity that may be tested or screened for a particular activity or property using the present invention.

If the target species is a toxin, the toxin may be selected from, but is not limited to, one or more toxins originating from animals, plants, or bacteria.

If the target species is a viral particle, the viral particle may be selected from, but is not limited to, one or more viral particles with and without a genome.

If the target species is a cell, the cell may be selected from, but is not limited to, one or more of pluripotent progenitor cells, human cells (e.g. B-cells, T-cells, mast cells, phagocytes, neutrophils, eosinophils, macrophages, endothelial cells), cancerous cells (e.g. those originating from liver, cervical bone, pancreatic, colorectal, prostate, epidermal, brain, breast, lung, testicular, renal, bladder cancers), unicellular organisms of non-human origin, algae, fungi, bacteria, plant cells, parasite eggs, plasmodia and mycoplasma.

If the target species is an organelle, the organelle may be selected from, but is not limited to, one or more of nucleus, mitochondria, Golgi apparatus, endoplasmic reticulum, lysosome, phagosome, intracellular membranes, extracellular membranes, cytoskeleton, nuclear membrane, chromatin, nuclear matrix and chloroplasts.

If the target species is a lipid, the lipid may be selected from, but is not limited to, one or more of signalling lipids, structural lipids, phospholipids, glycolipids and fatty acids.

If the target species is nucleic acid sequence, the nucleic acid sequence may be selected from, but is not limited to, one or more of DNA, cDNA, RNA, rRNA, mRNA, miRNA and tRNA.

If the target species is an oligosaccharide, the oligosaccharide may be selected from, but is not limited to, one or more of oligosaccharides of human, animal, plant, fungal or bacterial origin.

The target species may be any antigen or analyte that is indicative of a particular disease. The target may be selected from, for example, C-reactive protein (CRP protein), angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C-C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein; glucose; insulin; TRIG; GPT; HSPA1 B; IGFBP2; LEP; ADIPOQ; CCL2; ENG; HP; IL2RA; SCp; SHBG; and TIMP2. Currently preferred target species include a target species selected from the group consisting of CRP protein, insulin and a marker of one or more of neurodegeneration, cancer, myocardial infarction, diabetes and general trauma.

The target species may be a target associated with monitoring diabetes. In an embodiment, the target may be selected from glucose, insulin, Interleukin 2 receptor alpha (IL2-RA), C-reactive protein (CRP) and glycated hemoglobin (HbAlc). If the target species is glucose, the receptor may be selected from, for example, the molecular recognition element of GDH-FAD assay or a glucose/galactose binding protein ("GGBP") (Scholle, et al., Mol. Gen. Genet 208:247-253 (1987)). If the target is IL-2RA, the receptor may comprise or consist of a monoclonal antibody specific for IL-2RA. If the target species is or comprises C-reactive protein, preferably this is human C-reactive protein. If the target species is or comprises C-reactive protein, the receptor may comprise or consist of anti-CRP. If the target species is or comprises insulin, the receptor may comprise of consist of an insulin antibody.

By "disposed on the electrode surface" is meant that the association between the second moieties and the electrode surface is sufficiently stable that the second moieties do not become detached from the electrode surface in the presence of the carrier medium. The second moieties may be disposed on the electrode surface by covalent attachment or by non-covalent attachment. For the avoidance of doubt, it is emphasised that the association formed, for example, between a gold electrode surface and a thiol group comprised by a second moiety is regarded as being a covalent attachment. Indeed, this constitutes an exemplary means of disposing the second moieties on the electrode surface.

When the receptor is itself capable of becoming disposed on the electrode surface (i.e., of forming the stable association defined above), then the second moiety may consist of the receptor alone. For example, a receptor carrying a thiol group is inherently capable of forming a stable association with an electrode surface such as that of a gold electrode.

Alternatively, and preferably, the second moiety may be attached to the surface of the substrate via a linker species. If a linker species is present on the surface of the substrate, the linker species may for example comprise a self-assembling monolayer or may comprise a self-assembling monolayer-anchored polymer.

In an embodiment, the second moiety is of the formula $A_2$-$L_2$-REC, wherein $A_2$ is a moiety bound to the surface of the substrate, $L_2$ is a linker moiety and REC is the receptor (e.g., as defined elsewhere herein).

$A_2$ may be selected from any appropriate binding group, for example it may be selected from any of the groups exemplified herein with reference to $A_1$. For the avoidance of doubt, however, it is emphasised that the groups $A_1$ and $A_2$ may be the same or different in a particular electrode of the present invention.

$L_2$ may be any species that links to $A_2$ and also links to REC. In this context "links" includes "covalently links" and "non-covalently links", for example via a stable hydrophobic interaction. Furthermore, "links" implies a stable linkage between any two respective groups, wherein stable means that the linkage does not break in the presence of the carrier medium (e.g, a liquid medium, such as a biological fluid selected for example from blood, urine, tears, saliva, sweat, and cerebrospinal fluid). In one preferred embodiment, $L_2$ is covalently linked both to $A_2$ and to REC, i.e. it covalently links $A_2$ to REC. In an alternative preferred embodiment, $L_2$ is non-covalently linked to REC via a hydrophobic interaction (which is stable, as defined above). In this alternative preferred embodiment, $L_2$ is covalently linked to $A_2$. One example of a suitable stable hydrophobic interaction is that formed between an antibody receptor REC (e.g., anti-CRP) and a hydrocarbon moiety $L_2$. For the avoidance of doubt, a second moiety as defined herein includes a moiety comprising a linker species that is linked (e.g. covalently) to the electrode surface and which is associated with a particular receptor via a hydrophobic interaction, wherein that receptor also forms hydrophobic interactions with one or more other local second moieties.

$L_2$ is preferably a species that allows formation of a self-assembling monolayer. Examples of such species include those exemplified herein with reference to $L_1$. For the avoidance of doubt, however, it is emphasised that the groups $L_1$ and $L_2$ may be the same or different. Indeed, in a preferred embodiment the groups $L_1$ and $L_2$ are different.

In another embodiment, the second moiety may comprise a polymer that is attached both to: (a) the surface of the electrode; and (b) the receptor. Examples of such polymers include those exemplified herein in the context of the first moiety, e.g. the polymers comprising a plurality of betaine groups as defined herein.

The first moiety and the second moiety are typically functionally distinct, e.g. they are different (i.e., they have different chemical structures). For example, the first moiety may comprise no receptor that is capable of binding selectively to the target species. For example, the second moiety may comprise no redox active probe. Preferably, the first moiety does not comprise a receptor that is capable of binding selectively to the target species and the second moiety does not comprise a redox active probe. Where both the first and second moieties comprise linker species, these linker species are preferably different.

Preferably, the ratio of first moieties to second moieties disposed on the surface of the electrode is from 99:1 to 55:45, for example from 99:1 to 60:40. More preferably, the ratio of first moieties to second moieties disposed on the surface of the electrode is from 99:1 to 75:25, for example from 95:5 to 75:25 or from 90:10 to 80:20.

Preferably the ratio of the number of redox active probes that are associated with the electrode surface to the number receptors that are associated with the electrode surface and that are capable of binding selectively to the target species is from 99:1 to 55:45, for example from 99:1 to 60:40. More preferably, this ratio is from 99:1 to 75:25, for example from 95:5 to 75:25 or from 90:10 to 80:20.

One significant advantage of the design of the present electrode, i.e. the presence of discrete disposed first and second moieties, is that it enables preparation of an electrode in which the disposed redox active probes are present in substantial excess compared with the disposed receptors. This is believed to give rise to significantly improved signal levels, and thus sensitivity to target species, compared with, for example, a hypothetical method utilising the electrochemical methodology of the present invention in combination with an electrode having an equal number of disposed redox active probes and receptors.

Preferably, the electrode, as a whole (i.e, having the disposed first and second moieties), is selective for the target species. If the electrode is selective for the target species, this indicates that substantially only or only the target species will bind to the electrode (via binding to the receptors), and other species (e.g., present in the carrier medium with the target species) will not bind, or not bind to any significant degree, to other parts of the electrode or other species thereon. Such selective electrodes may be termed "highly selective electrodes". Selective for the target species means having a binding constant to the target species at least 50 times greater than the binding constant to any other species present in the carrier medium, preferably at least 100 times greater and more preferably still at least 200 times greater.

The electrode may also comprise moieties other than the first and second moieties which are also disposed on its surface. Typically any such moieties are not redox active in the redox window characterising the redox active probe. Typically any such moieties also are not capable of selectively binding to the target species. One example of moieties other than the first and second moieties that may be disposed on certain electrodes arises where the second moieties comprise linker species that are associated with the receptor via hydrophobic interactions. As explained in more detail below, such electrodes may be constructed in a method that comprises first disposing linker species on the electrode, followed by exposing the electrode to receptor molecules. It will be appreciated that in this instance, some of the disposed linker species may not be associate with receptors in the final electrode product (though it is of course essential that at least some of the disposed linker species do associate with receptors via the hydrophobic interactions, thereby generating second moieties).

Figure 1:
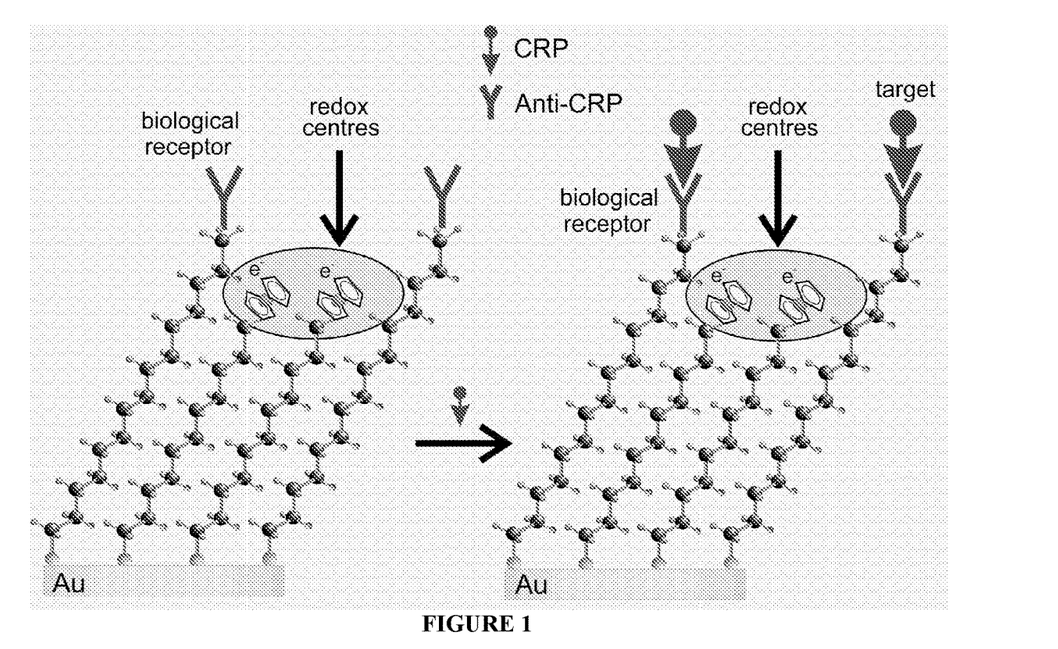
FIG. 1 depicts a schematic illustration of one exemplary system of the present invention, which is for detection of CRP protein using an electrode on which are disposed first moieties comprising ferrocene probes and second moieties comprising anti-CRP antibody receptors.

For ease of understanding, one exemplary electrode of the present invention is shown schematically in FIG. 1. The present invention is of course not limited to the specific construction details of this exemplary electrode.

The present invention also relates to an electrochemical spectrometer, wherein the spectrometer comprises an electrode as defined herein. The electrochemical spectrometer may be an electrochemical impedance spectrometer, for example an electrochemical impedance spectrometer of a standard design. The electrochemical spectrometer may comprise an electrode of the present invention as a working electrode, a counter electrode, and, if desired a reference electrode. The electrochemical spectrometer preferably comprises a means for applying, controlling and varying a potential between the working and counter electrodes, and a means for measuring the resultant current. The electrochemical spectrometer preferably comprises a potentiostat for controlling the potential and measuring the resultant current. The electrochemical spectrometer may comprise a means for calculating electron transfer resistance of the working electrode.

The electrochemical spectrometer preferably comprises a means for calculating impedance data from the potential applied and the resultant current. The electrochemical spectrometer may comprise a means for calculating capacitance and/or resistance terms from the said impedance data; preferably such terms are directly related to purely faradaic activity such redox capacitance.

The present invention also relates to the use of an electrode as described herein, or an electrochemical spectrometer as described herein, for the detection of a target species. The use may include detecting the presence of and/or detecting the concentration of the target species.

Method of Making the Electrode

The electrode as described herein may be made by disposing, on the surface of an electrode substrate, (i) first moieties that each comprise a redox active probe and (ii) second moieties that each comprise a receptor capable of binding selectively to a target species.

The method of making the electrode may for example comprise reacting the electrode substrate with (I) first reagent molecules for providing said first moieties and (II) second reagent molecules for providing said second moieties.

The structure of the first and second reagent molecules is governed by the specific reaction methodology being employed to produce the electrode. Methods of providing the first moieties include, for example:

(1A) Disposing the first moieties directly on the electrode substrate, wherein each first moiety itself comprises a functional group that is capable of forming a stable association with the electrode substrate (e.g., the functional groups defined already herein as $A_1$). Note that in this embodiment the first reagent molecules consist of the first moieties (i.e., the first moieties are the first reagent molecules). Thus, the first reagent molecules each comprise a redox active probe and they are also capable of becoming disposed on the surface of the electrode substrate. Examples of such first reagent molecules include the first moieties as defined elsewhere herein.

(1B) Disposing first reagent molecules on the surface of the electrode substrate, then attaching redox active groups to the first reagent molecules. In this embodiment, the first reagent molecules are capable of (a) becoming disposed on the surface of the electrode substrate and (b) attaching to the redox active groups. The first reagent molecule may be capable of attaching to a redox active group via a suitably designed functional group on the first reagent molecule (i.e, one capable of reaction with a corresponding functional group on the redox active group of interest). The method may comprise activating the first reagent molecules disposed on the surface of the electrode substrate, e.g. by reaction with an activator, such as N-hydroxysuccinimde (NHS), to allow for facile attachment of the redox active groups to the disposed first reagent molecules.

Similarly, methods of providing the second moieties include, for example:

(2A) Disposing the second moieties directly on the electrode substrate, wherein each second moiety itself comprises a functional group that is capable of forming a stable association with the electrode substrate (e.g., the functional groups defined already herein as $A_1$). Note that in this embodiment the second reagent molecules consist of the second moieties (i.e., the second moieties are the second reagent molecules). Thus, the second reagent molecules each comprise a receptor and they are also capable of becoming disposed on the surface of the electrode substrate. Examples of such second reagent molecules include the second moieties as defined elsewhere herein.

(2B) Disposing second reagent molecules on the surface of the electrode substrate, then attaching receptors to the second reagent molecules. In this embodiment, the second reagent molecules are capable of (a) becoming disposed on the surface of the electrode substrate and (b) attaching to the receptors. The second reagent molecule may be capable of attaching to a receptor via a suitably designed functional group on the second reagent molecule (i.e, one capable of reaction with a corresponding functional group on the receptor of interest). The method may comprise activating the second reagent molecules disposed on the surface of the electrode substrate, e.g. by reaction with an activator, such as N-hydroxysuccinimde (NHS), to allow for facile attachment of the receptors to the disposed second reagent molecules.

In one preferred aspect of the present invention, the method comprises adopting the above strategy (1A) in conjunction with the above strategy (2B), i.e. disposing the first moieties directly on the surface of the electrode substrate, disposing second reagent molecules on the surface of the electrode substrate, and then attaching receptors to the second reagent molecules.

The method of the present invention may comprise simultaneously reacting the electrode substrate with (I) the first reagent molecules for providing the first moieties and (II) the second reagent molecules for providing the second moieties. Alternatively, the method may comprise sequentially reacting the electrode substrate, in any order, with (I) the first reagent molecules for providing the first moieties and (II) the second reagent molecules for providing the second moieties. "In any order" means that the first reagent molecules may be reacted with the electrode substrate before the second reagent molecules are reacted with the electrode substrate or that instead the second reagent molecules are reacted with the electrode substrate before the first reagent molecules are reacted with the electrode substrate.

Preferably, however, the first reagent molecules and the second reagent molecules are reacted simultaneously with the electrode substrate. This makes it particularly easy to adjust the relative amounts of disposed first and second moieties in the electrode product, by suitable adjusting the concentrations of the first and second reagent molecules. For example, the concentration of the first and second reagent molecules may be from 99:1 to 55:45, for example from 99:1 to 60:40. More preferably, this ratio is from 99:1 to 75:25, for example from 95:5 to 75:25 or from 90:10 to 80:20.

In one particularly preferred aspect of the present invention, the method comprises: (a) simultaneously disposing on the surface of the electrode substrate first moieties and second reagent molecules that are capable of attaching to receptors; and then (b) attaching receptors to the second reagent molecules.

Preferably the method comprises forming a self-assembling monolayer, i.e. a mixed monolayer comprising both first moieties and second moieties.

Method for Electrochemical Detection of a Target Species

The method for electrochemical detection of a target species typically comprises at least the following steps:

(A) contacting a carrier medium comprising the target species of interest with an electrode as defined herein;

(B) obtaining a first measurement of complex impedance by electrochemical impedance spectroscopy at a first applied potential that is within the redox window of the redox active probe; and (C) obtaining a second measurement of complex impedance by electrochemical impedance spectroscopy at a second applied potential that is different from the first applied potential.

However, in an alternative embodiment the method may omit the step (C), i.e. it may involve obtaining only a single ("first") measurement of complex impedance. Typically this alternative embodiment is appropriate when the non-faradaic contribution to the overall electrochemical signal obtained in step (B) is negligible, e.g., when its magnitude is less than 20%, preferably less than 10%, more preferably less than 5% and most preferably less than 1% of the overall electrochemical signal (containing faradaic and non-faradaic contributions), as obtained at a particular applied potential and a particular EIS frequency (e.g., the applied potential and frequency at which the target concentration is to be quantitatively determined). The relative contributions of faradaic and non-faradaic components can be unambiguously confirmed by a skilled person for a particular electrode system by carrying out EIS measurements both within the redox window of the redox active probe (to obtain the overall signal) and outside the redox window of the redox active probe (to obtain the purely non-faradaic signal component, which, as explained further elsewhere herein, is insensitive to applied potential). Such an alternative embodiment may be appropriate, for example, when the quantity of redox active probe is in large excess to the quantity of receptors on the electrode surface.

In the method for electrochemical detection of a target species, the carrier medium is preferably in liquid form. The carrier liquid may be any liquid in which the target species can be suspended or dissolved. In an embodiment, the carrier liquid comprises water. In an embodiment, the carrier liquid comprises a biological fluid. A biological fluid may be a fluid that has been obtained from a subject, which may be a human or an animal. In an embodiment, the carrier liquid comprises an undiluted biological fluid. An undiluted biological fluid in the present context is a biological fluid obtained from a subject, e.g. a human or animal, that has not been diluted with another liquid. The biological fluid may be selected from blood, urine, tears, saliva, sweat, and cerebrospinal fluid.

Optionally, the carrier medium comprises a biological fluid obtained from a subject, e.g. a human or animal, and a diluent. The diluent may be added to the biological fluid after it has been obtained from the subject. The diluent may include a liquid medium, e.g. a liquid medium selected from water and an alcohol, e.g. an alcohol, e.g. ethanol. The carrier medium may further comprise a buffer. The buffer may comprise a phosphate.

The above steps (B) and (C) involve obtaining measurements of complex impedance by electrochemical impedance spectroscopy. Electrochemical impedance spectroscopy (EIS) is known to the skilled person. Generally, a varying ac potential is applied on a bias (or DC) potential between a working electrode and a counter electrode. Generally, EIS involves scanning across a range of ac frequencies. The ratio of the input signal (typically the varying potential) to the output signal (typically the varying current) allows the impedance to be calculated. There is generally a phase difference between the input signal and the output signal, such that the impedance can be considered as a complex function $Z^*$, having a real part (sometimes termed $Z'$) and an imaginary part (sometimes termed $Z''$).

The frequency range of the varying ac potential applied may be from 0.05 Hz to 10 kHz. The amplitude of the applied ac potential, which is typically in the form of a sine wave, may be from 1 mV to 100 mV, optionally from 5 mV to 50 mV, optionally from 5 mV to 20 mV, optionally from 5 mV to 15 mV, optionally 8 mV to 12 mV, optionally about 10 mV.

In an EIS method, the bias potential (or direct current potential) may be set at any desired value. However, the method of the present invention involves carrying out two separate measurements at specifically chosen potentials. Specifically, the first applied potential is within the redox window of said redox active probe. Furthermore, the second applied potential is different from the first applied potential. As explained in more detail below, this ensures that the relative amounts of faradaic and non-faradaic (herein also described as "parasitic") contributions to the signal are different. Consequently, comparison between the signals obtained at the first and second applied potentials, respectively, enables the non-faradaic contributions to be quantified and eliminated.

In the method of the present invention, quantification of the concentration of the target species is achieved by analysis of the faradaic contribution to the overall electrochemical signal. It is therefore desirable to carry out the respective measurements (i.e., at the first and second applied potentials) such when the non-faradaic component is eliminated, this results in the minimum amount of simultaneous elimination of faradaic contribution to the signal. The inventors have found that this can be achieved when:

(a) the first applied potential is the half wave potential of the redox active probe (this maximises the faradaic contribution to the signal obtained in the EIS measurement at the first applied potential); and (b) the second applied potential is a potential that is outside the redox window of the redox active probe (this means that the signal obtained in the EIS measurement at the second applied potential is purely non-faradaic, and therefore that a simple subtraction of signals corresponding to the first and second applied potentials exclusively involves elimination of the non-faradaic contribution and does not involve any elimination of the faradaic contribution obtained at the first applied potential).

The remaining faradaic signature includes that which is capacitative—redox capacitance. This can be used as a transduction of interfacial binding.

Preferably, therefore, the first applied potential is the half wave potential of the redox active probe and the second applied potential is a potential that is outside the redox window of the redox active probe.

Typically, the method of the invention involves calculating the concentration of the target species from the first and second measurements. This step typically comprises, first, eliminating non-faradaic contributions to the measurements and, second, calculating the concentration of the target species from the resulting (purely faradaic) contributions to the measurements.

In more detail, the method of the invention preferably comprises a step of converting the first measurement of complex impedance into a first measurement of the complex capacitance, and converting the second measurement of complex impedance into a second measurement of the complex capacitance. As is well known in the art, this conversion can be carried out by measuring, in a standard practical EIS analysis, the complex impedance function $Z^*(\omega)$, sampled across a range of frequencies $\omega$ at a particular potential, and converting it phasorially into complex capacitance $C^*(\omega)$ with its real and imaginary components, using the equation $C^*(\omega)=1/i\omega Z^*(\omega)$.

The first measurement of the complex capacitance may comprise a first measurement of the real component of the complex capacitance, a first measurement of the complex component of the complex capacitance, or both a first measurement of the real component of the complex capacitance and a first measurement of the complex. component of the complex capacitance. Preferably the first measurement of the complex capacitance comprises or consists of a first measurement of the real component of the complex capacitance.

Similarly, the second measurement of the complex capacitance may comprise a second measurement of the real component of the complex capacitance, a second measurement of the complex component of the complex capacitance, or both a second measurement of the real component of the complex capacitance and a second measurement of the complex. component of the complex capacitance. Preferably the second measurement of the complex capacitance comprises or consists of a second measurement of the real component of the complex capacitance.

In a particularly preferred embodiment, first and second measurements of the real component of the complex capacitance are thereby obtained.

The imaginary component of the complex capacitance, C", plotted against sampling frequency, resolves the timescale of non-faradaic contributions to the electrochemical response (these being insensitive to the applied potential). So too does the real component of the complex capacitance, C', plotted against sampling frequency.

This in turn enables a simple elimination of non-faradaic contributions through the acquirement of data collected, for example, with the electrode poised outside the redox window and then with the electrode poised in the redox window of the redox active agent.

Figure 5:
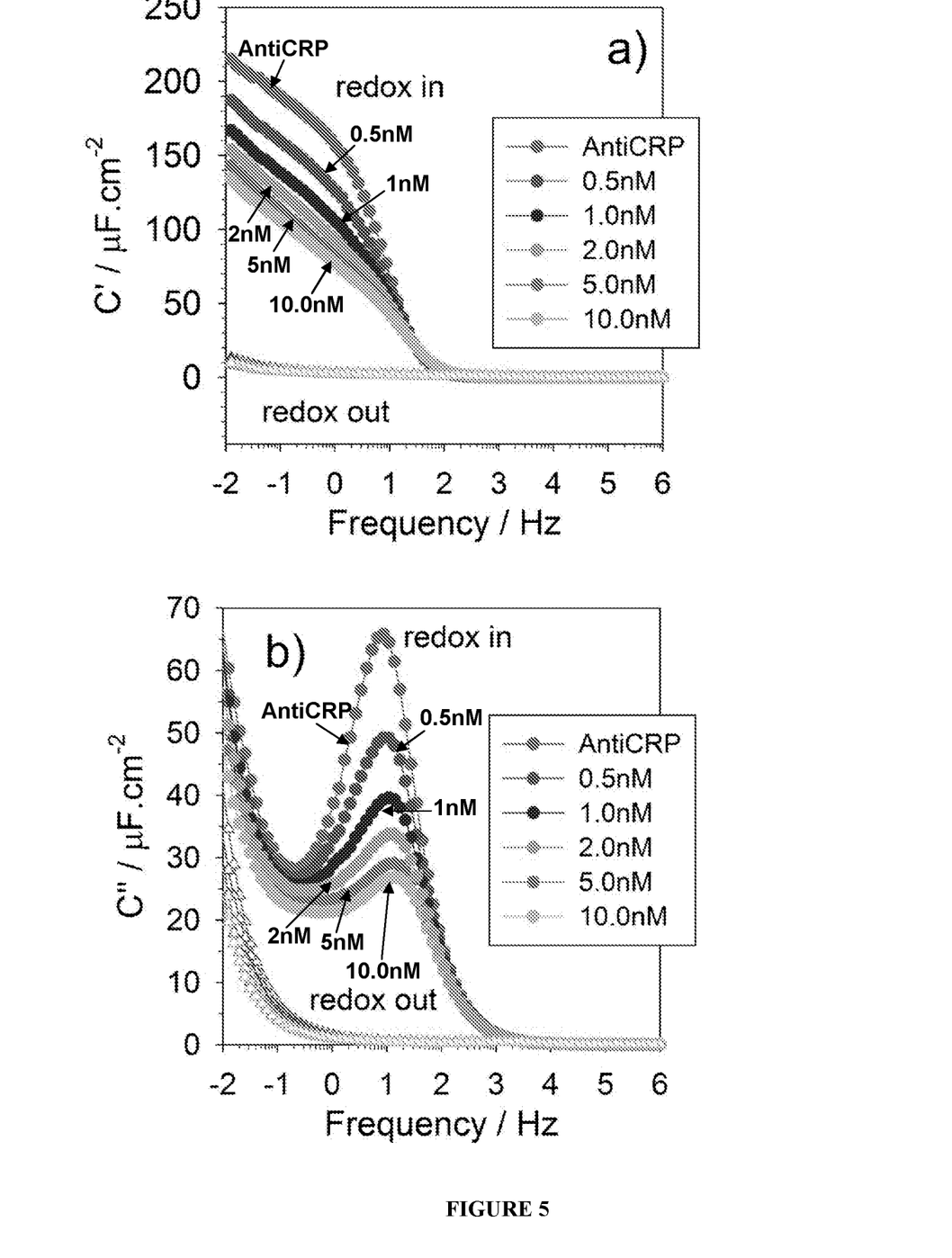

To assist in understanding this principle, reference may be made to the specific embodiment of the present working Example. Note in particular that FIGS. 5a) and 5b) show the real and imaginary components of the complex capacitance, C' and C", respectively, plotted against sampling frequency, for a series of "redox in" experiments (at different target species concentrations, and where "redox in" represents the half wave potential of the ferrocene redox active probe in the specific electrode being used), as compared against an analogous series of a series of "redox out" experiments (where the applied potential was outside the redox window of the ferrocene redox active probe). In the "redox in" experiments, the total signal contains contributions from both faradaic (sensitive to applied potential) and non-faradaic (insensitive to applied potential) processes. In the "redox out" experiments, the total signal corresponds exclusively to non-faradaic processes.

The method of the invention thus preferably further comprises subtracting the second measurement of the real component of the complex capacitance from the first measurement of the real component of the complex capacitance, thereby eliminating non-faradaic contributions to the electrochemical response of the system and obtaining a measurement of the "redox capacitance" of the system. Redox capacitance represents the exclusively faradaic component of the real component of the complex capacitance.

Further details on the methodology for extracting a redox capacitance measurement of a system comprising a specific electrode and a specific carrier medium (containing a specific amount of target species) can be found in Bueno et al., J. Phys. Chem. B 2012, 116, 8822-8829, the content of which is herein incorporated by reference in its entirety. This document describes the basic theoretical principles of the capacitance spectroscopic technique used in the method of the present invention and explains in detail how to obtain a measurement of redox capacitance for a generic redox-active electrode. It can be emphasised, however, that Bueno et al. do not disclose or suggest that the capacitance spectroscopic technique would be effective for quantitatively analysing the effect of a target species on a surface-confined receptor species on such a surface.

The method of the present invention typically involves calculating the concentration of the target species from the change in redox capacitance occurring upon binding of the target species to the second moieties. The present inventors found that capacitance spectroscopy provides an exceptionally sensitive probe of the biorecognition event occurring between an electrode-confined receptor and a target species in a carrier medium, when the electrode further comprises confined redox active probes. Although not wishing to be bound by theory, it appears that redox capacitance is extremely sensitive to the small changes in local environment occurring when a target species binds to the electrode-confined receptors. An illustration of the highly sensitive nature of the method of the present invention is provided in the present Example, which clearly demonstrates that performing capacitance spectroscopy using an electrode of the present invention generates substantially better results (i.e. greater sensitivity and selectivity) than when using voltammetric data, for example from conventional cyclic voltammetric analysis.

The concentration of the target species may be calculated from the redox capacitance obtained at any frequency sampled during the EIS measurements. Typically, the concentration of the target species is calculated from the redox capacitance obtained at a frequency in which the first measurement of the real component of the complex capacitance is close to or at its maximum magnitude.

The measurements giving rise to calculation of the concentration of the target species are thus associated with a specific frequency, which is characteristic of the identity of the redox active probe. It will therefore be appreciated that the methods and electrodes of the present invention are readily multiplexable. In particular, a multiplex strategy can be applied wherein simultaneous detection of different target species is possible, by making using of electrodes that have different receptors and different redox active probes, whose electrochemical responses to an applied potential peak at different frequencies. By frequency-resolving the resulting multiplexed data, simultaneous analysis of multiple target species becomes possible.

The method of the invention may alternatively comprise subtracting the second measurement of the imaginary component of the complex capacitance from the first measurement of the imaginary component of the complex capacitance (i.e., as opposed to using the respective real components), thereby eliminating non-faradaic contributions to the electrochemical response of the system in the final "subtraction result". Again, the subtraction result represents the exclusively faradaic component of the imaginary component of the complex capacitance. The concentration of the target species may then be calculated from the subtraction result obtained at any frequency sampled during the EIS measurements. Typically, the concentration of the target species is calculated from the subtraction result obtained at a frequency in which the first measurement of the imaginary component of the complex capacitance is close to or at its maximum magnitude.

The concentration of the target species may be calculated by comparing the data obtained for a carrier medium containing an unknown concentration of target species with data obtained for carrier media containing known concentrations of target species.

In the alternative embodiment of the method in which the step (C) is omitted, the concentration of the target species can be obtained from the single ("first") complex impedance measurement, e.g. via conversion of the complex impedance to a complex capacitance and then obtaining the concentration of the target species from a value of either the real or imaginary component of the complex capacitance at a chosen frequency. In this alternative embodiment, the presence of negligible non-faradaic contribution to the overall electrochemical signal means that the above-described second measurement step, and the subtraction step, are not required.

In the present invention, the concentration of the target species in the carrier medium may be 0.1 pM or more, optionally 0.2 pM or more, optionally 0.5 pM or more, optionally 1.0 pM or more. The concentration of the target species in the carrier medium may be 100 nM or less, optionally 80 nM or less, optionally 50 nM or less, optionally 10 nM or less. The concentration of the target species in the carrier medium may be from 0.1 pM to 100 nM, optionally from 0.2 pM to 100 nM, optionally from 0.5 pM to 50 nM.

It is also possible to regenerate the electrode that has been bound to target species by dissociating bound target species from the electrode. The method may therefore involve, after contacting the electrode with the carrier medium such that target species is bound to the receptors, dissociating target species from the receptors. The dissociating may comprise contacting of the electrode surface having target species thereon with an acidic liquid medium, optionally having a pH of 6 or lower, optionally a pH of 5 or lower, for example a pH of 4 or lower. The acidic liquid medium may contain an acidic substance, for example an acidic buffer (for example, glycine hydrochloride). The acidic liquid medium may be aqueous or non-aqueous. For example, it may be a non-aqueous medium comprising a non-aqueous solvent such as DMSO.

The method may further comprise, after dissociating target species from the receptors, reusing the electrode in one or more further methods of the present invention.

Methods and electrodes provided herein are described below with reference to the particular Example. The invention is not intended to be limited to this particular Example.

EXAMPLE

Experimental Procedures and Methods

Gold electrodes disks (2.0 mm diameter, Metrohm) were mechanically polished with decreasing particle sizes aluminum oxide pads (1 µm, 0.3 µm and 0.05 µm). Sonication in water, to remove adhered particles, was performed between polishing. Electrodes were then electrochemically polished in deaerated NaOH 0.5 M (−1.5 V and −0.5 V at a scan rate of 100 mV s$^{-1}$), then deaerated 0.5 M H$_2$SO$_4$ (−0.2 V and 1.5 V at a scan rate of 100 mV s$^{-1}$) until the gold reduction peak in CV stabilizes (around 50 cycles). After electrochemical polishing the electroactive areas were evaluated by integration of the cathodic peak from gold electropolishing voltammograms and converted to the real surface area using a conversion factor of 400 µC cm$^{-2}$. Finally, the polished gold electrode was characterized by Cyclic Voltammetry (CV) and Capacitance Spectroscopy (CS).

Electrochemical measurements were performed with an Autolab potentiostat model PGSTAT30 using a three-electrode configuration with Ag/AgCl (3 M in KCl) as a reference, platinum mesh as a counter, and functionalized gold electrode as the working electrode.

The test electrode of the invention ("test electrode") was generated as follows. Mixed Self-Assembled Monolayers (SAM) were generated by incubation of freshly cleaned gold electrodes in a solution of 0.2 mM pentadecanethiol and 2.0 mM 11-Ferrocenyl-Undecanethiol in ethanol for 16 h, prior to washing in alcohol, deionized water and drying under nitrogen. Receptive surfaces were prepared by immersion of these in 1 µM of Anti-CRP in 0.1 M bicarbonate buffer, pH 8.5 prior to analysis by Capacitance Spectroscopy and CV.

C-Reactive Protein (CRP) aliquots (20 µl) were added to the interface with concentrations ranging from 0.5 nM to 10.0 nM in PBS (pH 7.4).

Impedance Derived Capacitance Spectroscopy Approach

The AC frequencies for impedance experiments ranged from 1 MHz to 10 mHz, with an amplitude of 10 mV. All the obtained impedance data were checked regarding compliance with the constraints of linear systems theory by Kramers-Kronig using the appropriate routine of the FRA AUTOLAB software. Impedance data were acquired at half wave potential/redox in (ca. 0.5V) and redox out (ca. 0.1 V) regions (see also FIG. 2). Modulation frequencies were varied in 80 steps from 0.1 mHz to 10 MHz.

The complex $Z^*(\omega)$ (impedance) functions at the two potentials were converted into $C^*(\omega)$ (capacitance) functions. A redox capacitance approach was then performed to compare maximum and minimum faradaic activity. The resulting FRA data were processed and treated to obtain the real components of the complex capacitance at each potential and the functions subtracted to obtain the redox capacitance of the system.

Negative Controls and Non-Receptive (Pure Ferrocene) Films

A negative control was performed by testing the electrode response in the absence of CRP.

A second control experiment was carried out by testing an electrode functionalised only with the ferrocene layer (i.e., no discrete anti-CRP layer was created). This pure ferrocene-functionalised electrode was subsequently incubated with CRP target in order to demonstrate that anti-CRP is required for a change in reporting redox capacitance signal, i.e. that the response is specific to a specific receptor-target interaction.

Figure 2:
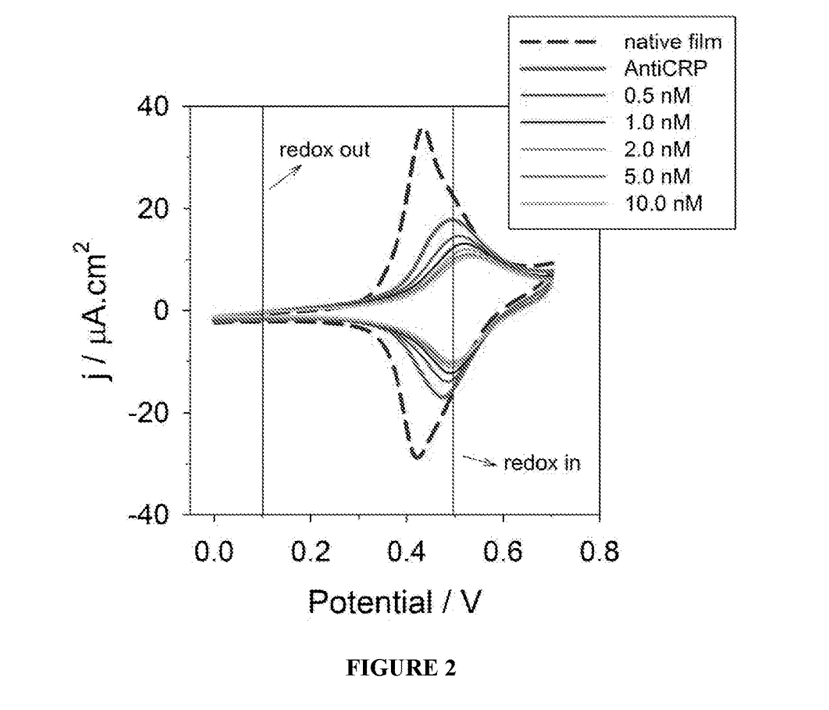
FIG. 2 depicts CV-resolved perturbations in faradaic activity of a redox active, CRP-recruiting molecular film in the presence of different target concentrations at a scan rate of 100 mVs$^{-1}$, as further described in the Example (note that progressively smaller areas enclosed by the lines correspond to progressively increasing target concentrations). All plotted curves are mean values of three different working electrodes. The "redox in" and "redox out" lines denote potential regions where capacitance spectroscopy was performed, as described in more detail in the Example.

Results: CV Response, Including Comparison with Negative Control and Ferrocene Pure Layer CV measurements were carried out at a range of CRP concentrations, as shown in FIG. 2. The scan rate was 100 mVs$^{-1}$. A first test was carried out on a "native film" which corresponds to the test electrode but prior to association with the film of the anti-CRP antibody. The next text was carried out on the finished test electrode ("AntiCRP"); it can be sent that the initial on-film assembly of antibody is associated with both an anodic shift and drop in response of the "native film" to levels which, in the absence of CRP, are thereafter stable. Subsequent CRP binding results in a progressive change in response as concentration changes. All plotted curves are mean values of three different working electrodes.

Figure 3:
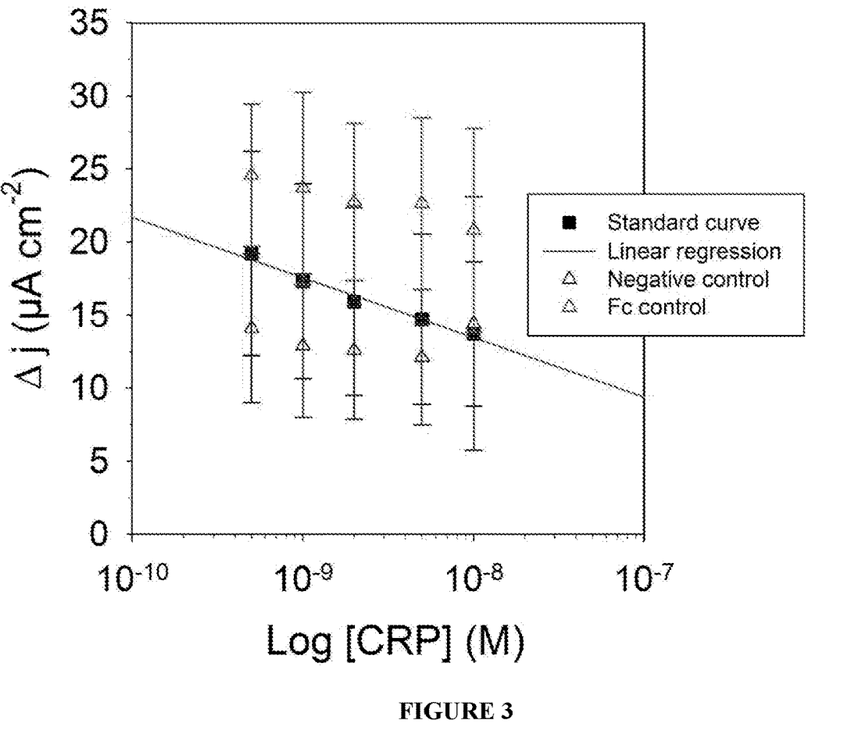
FIG. 3 depicts the comparative response of voltammetric peak currents obtained using the test electrode of the Example, as well as the results of comparative studies corresponding to a "negative control" (where no CRP was present in the carrier medium; lower group of triangles) and to an electrode modified purely with ferrocene moieties (even after incubation process on AntiCRP solution; "Fc control"; higher group of triangles). The Pearson linear coefficient is higher than 99% between the current component and the logarithmic of CRP concentration, but controls, in the absence of specific target, have the same sensitivity.

The comparative response of voltammetric peak currents from CV for the test electrode relative to the negative control system and the "pure ferrocene" electrode was also tested. The results are shown in FIG. 3, from which it is clear that this is a relatively insensitive and unselective indicator of biorecognition. Being neither frequency resolved nor a clean function of any single electrochemical process (a composite of capacitance and resistance terms), this approach was concluded to be less useful than that based on redox capacitance.

Results: Redox Capacitance Analysis

Figure 4:
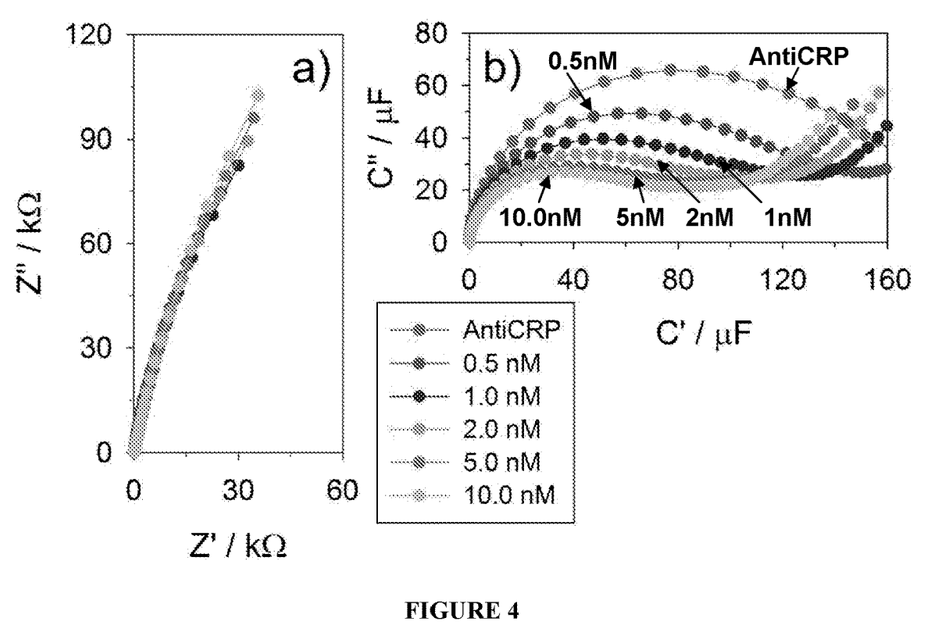
FIG. 4 depicts initial impedance analyses resolving the unresponsiveness of interfacial impedance and the sensitivity of capacitance, respectively, for the test electrode of the Example. Graph a) shows a Nyquist impedimetric plot of Z" versus Z' for a redox-active, CRP-receptive film, where only minimal sensitivity to target binding is evident. The analogous capacitative response to CRP binding is shown in graph b), where a modulation in response to CRP is observed (at C'=80 µf, progressively lower lines on the graph corresponding to progressively increasing target concentrations). All plots are average curves obtained from three different working electrodes.

Initial impedance analyses, resolving the unresponsiveness and sensitivity of interfacial impedance and capacitance respectively, are shown in FIG. 4. Graph a) shows Nyquist impedimetric plot of Z" versus Z' for the test electrode, where only minimal sensitivity to target binding is evident. On the other hand, the analogous capacitative response to CRP binding is shown in graph b), where a modulation in response to CRP is observed (obtainable from the semicircle diameters).

The interfacial impedance is insensitive to CRP binding regardless of the potential poise of the underlying electrode. This unresponsiveness is believed to arise because the impedimetric characteristics probed are confined to the thin layer of the film, rather than by interactions of the film with a solution phase redox probe. The planting of the redox reporter within the film, means that, by design, its transduction is capacitative (probed impedance is unresponsive, probed capacitance is dominated by the redox sites and dependent on local dielectric environment).

Bode plots of the redox in and redox out tests, at various CRP concentrations, are shown in FIG. 5. The film redox activity is cleanly resolved through capacitance. Specifically, on initially poising the electrode at the half wave potential of the ferrocene surface probe, the transducing signal was maximised. On subsequent exposure of such surfaces to low levels of CRP, a notable decrease in faradaic activity was observable. These changes equate to a change in redox site activity and a detectable degree of redox capacitance discharging (the redox component of the film is engaged in less Faradaic activity).

The capacitative trends are initially clearly frequency resolved in the Bode plots, where it is evident that capacitance outside of the redox window is both small and unresponsive to target binding. An analogous capacitance analysis at potentials that charge the ferrocene ("redox in") is, clearly, highly responsive to CRP concentration.

Figure 6:
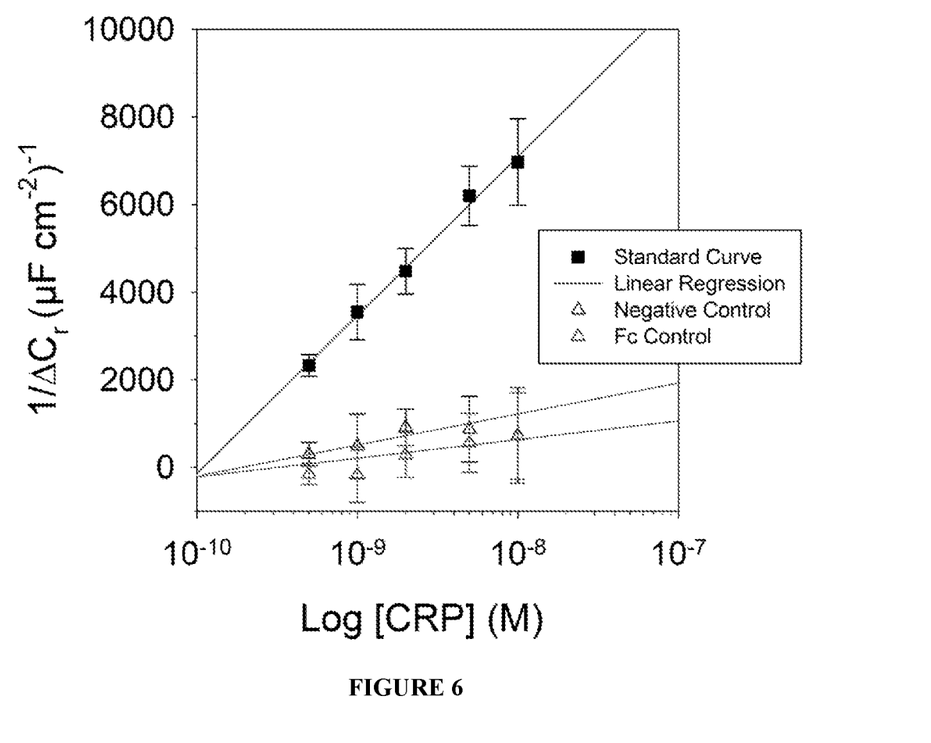
FIG. 6 depicts capacitive analytical curves acquired at 8 Hz with receptive and redox active molecular films (shown as filled squares), as further described in the Example. Also shown are both the unresponsiveness of mixed film charging in the absence of CRP (the negative control) and the unresponsiveness of a 100% ferrocene layer to different CRP target concentration (Fc control—lowest line on the graph). The Pearson linear coefficient is higher than 99%.

The redox capacitive response were extracted specifically from the real components using the methods described herein and used in the generation of sensitive and frequency optimized (here 8 Hz) analytical curves. The results are shown in FIG. 6. Also clearly evident from this Figure is the selectivity of the interfacial charging response to CRP (there is no response to the negative control protein or of the redox capacitance to CRP when no antibody receptor is present).

From these analyses, the L.O.D (limit of detection), L.O.Q (limit of quantification) and percentage sensitivity per decade were, respectively, 200 pM, 600 pM and 95% obtained according to IUPAC standardization.

The invention claimed is:

1. An electrode for use in the electrochemical detection of a target species, the electrode comprising an electrode surface on which first moieties and second moieties are disposed,
   wherein said first moieties and said second moieties are separate moieties and wherein each of said first moieties comprises a redox active probe and each of said second moieties comprises a receptor capable of binding selectively to said target species; and
   wherein the ratio of first moieties to second moieties disposed on said surface of said electrode is from 95:5 to 75:25.

2. An electrochemical spectrometer comprising an electrode of claim 1.

3. The electrode according to claim 1, wherein said redox active probe is ferrocene.

4. The electrode according to claim 1, wherein said receptor is selected from the group consisting of antibodies, antibody fragments, aptamers, oligosaccharides, peptides and proteins.

5. The electrode according to claim 1, wherein said target species is selected from the group consisting of CRP protein, insulin and a marker of one or more of neurodegeneration, cancer, myocardial infarction, diabetes and general trauma.

6. The electrode according to claim 1, wherein said first moieties have the formula $A_1$-$L_1$-RAP, wherein $A_1$ is a moiety bound to the surface of the electrode, $L_1$ is a linker moiety and RAP is said redox active probe.

7. The electrode according to claim 1, wherein said second moieties have the formula $A_2$-$L_2$-REC, wherein $A_2$ is a moiety bound to the surface of the electrode, $L_2$ is a linker moiety and REC is said receptor.

* * * * *